United States Patent
Rittenburg et al.

[11] Patent Number: 6,068,981
[45] Date of Patent: May 30, 2000

[54] MARKING OF ORALLY INGESTED PRODUCTS

[75] Inventors: James H. Rittenburg, Perkasie, Pa.; Frank G. Angella, Singapore, Singapore; Michael G. Pappas, Shrewsbury, Mass.

[73] Assignee: Biocode, Inc., Cambridge, Mass.

[21] Appl. No.: 08/943,639

[22] Filed: Oct. 3, 1997

[51] Int. Cl.$^7$ .......................... A61K 49/00; G01N 33/48; G01N 33/53

[52] U.S. Cl. .......................... 435/7.1; 424/9.1; 424/457; 424/468; 436/56; 436/63; 436/172; 436/501; 436/822; 514/811; 514/812; 514/964; 800/3

[58] Field of Search .......................... 424/9.1, 457, 468; 435/7.1; 436/56, 63, 172, 501, 822; 514/811, 812, 964; 800/3, 8

[56] References Cited

U.S. PATENT DOCUMENTS

| | | | |
|---|---|---|---|
| 4,622,244 | 11/1986 | Lapka et al. | 514/811 |
| 4,861,588 | 8/1989 | Neurath et al. | 530/324 |
| 4,953,562 | 9/1990 | Rosen et al. | 436/56 |
| 5,039,616 | 8/1991 | Copelan | 436/56 |
| 5,179,027 | 1/1993 | Fisher | 436/56 |
| 5,210,040 | 5/1993 | Jou et al. | 436/528 |
| 5,429,952 | 7/1995 | Garner et al. | 436/822 |
| 5,505,967 | 4/1996 | Geary et al. | 424/497 |

*Primary Examiner*—David Saunders
*Attorney, Agent, or Firm*—Clark & Elbing LLP

[57] ABSTRACT

A method of monitoring a therapeutic regimen in an animal, the method involving a) providing to the animal a therapeutic compound and a detectable compound that passes into the bloodstream, excretory system, or other tissue or body fluid in detectable form; b) after a period of time, following step (a), sufficient for passage of a detectable amount of the detectable compound into the body fluid or tissue, collecting a sample of the fluid or tissue from the animal; and c) measuring or detecting the detectable compound, or a detectable metabolite thereof, in the sample, wherein the detectable compound involves one member of a specific binding pair, and detection is carried out using the second member of the specific binding pair.

26 Claims, No Drawings

MARKING OF ORALLY INGESTED PRODUCTS

BACKGROUND OF THE INVENTION

The invention relates to monitoring oral administration of pharmaceuticals in animals and humans, e.g., monitoring self-administration of pharmaceuticals in human patients.

A major problem in optimal drug administration is patient compliance. In clinical trials of new drugs, and in normal treatment regimens with approved drugs, it is important to establish that patients are complying with prescribed treatment programs. In clinical trials, lack of compliance compromises the data developed in support of new drug development, and can result in discontinuation of development programs for potentially useful drugs. Conducting these human trialls carefully and accurately is crucial since these data will be relied on to save lives. In addition, conducting these trials efficiently is important because this step is a very expensive and time consuming part of bringing a drug from the discovery stage to the bedside.

For commercially available drugs, lack of compliance may cause a physician subsequently to over-prescribe a treatment or switch to another, possibly less effective, treatment. In addition, lack of compliance in patients with communicable diseases can threaten the public health. For example, tuberculosis is on the rise at least in part because many patients fail to complete an established effective treatment course. Patients will skip doses, take them at the wrong time intervals, or take multiple doses at a time, especially when they are about to visit their physician. Society, to avoid a public health disaster, is forced to send nurses door to door simply to ensure that patients have actually swallowed their pills. Ideally, such precious medical resources would be better utilized as more than just "pill police."

In other cases, where drug and alcohol abusers are placed on specific treatment regimens, it is critical that the medication is taken faithfully. To that end, methadone patients are required to come to a clinic daily to ensure that the treatment is administered. The availability of better methods for compliance monitoring would provide physicians with a tool that would allow them to give patients greater responsibility in administering their own treatment, reducing health care costs and improving the quality of life of the patient. In the case of methadone, a means for differentiating legal methadone from illegal opiates would be very useful.

Ideally, compliance with treatment regimens includes both taking the proper amount of medication (no more, no less) and taking it at the correct time intervals (evenly spaced). This assures that levels of the medication in the bloodstream will remain consistent, allowing the drug to perform optimally.

Assay methods are sometimes used to monitor patients for compliance to assure that they are taking medication as prescribed. Assay methods that would detect a patient-ingested marker over a period of time longer than 24 hours would be particularly useful for physicians and healthcare workers when they see their patients at widely spaced intervals. Presently, no such methods exist.

One report in the literature of the use of a labelling compound to monitor therapeutic regimen compliance is Publication RV31899 (1995) from duPont de Nemours Co., manufacturers of the drug Naltrexone, used to treat alcohol dependence. The duPont product monograph states: "Subjects were prescribed 50 mg/d of REVIA™ [Naltrexone] or placebo Riboflavin, 25 mg was also incorporated into all capsules to evaluate patient compliance. Urine samples were inspected biweekly using a UV light to detect the presence of riboflavin. This is an example of a crude, qualitative method to determine the degree of patient compliance with Naltrexone treatment. Riboflavin concentrations of 1.5 $\mu$g/ml or greater were considered positive, as less than 1.5 $\mu$g/ml of urinary riboflavin is typically observed with a normal diet.

Another concern arises in the testing of athletes, employees, and patients for drug abuse, where questions can arise whether urine samples have been switched or altered (diluted).

Finally, it is often important in animal husbandry to ensure that livestock have consumed certain foods or veterinary products, from concern both for the health of the animal, and for the wholesomeness and safety of the food products derived from the animal.

SUMMARY OF THE INVENTION

The invention provides means for marking orally ingested or injected products to enable subsequent confirmation and monitoring of the marked product; the invention is useful, e.g., to ensure compliance with oral administration regimens of pharmaceuticals. While one important objective of the invention is to provide enhanced methods for drug monitoring, in its broadest sense the invention encompasses the uptake or intake of a detectable compound, or marker, by any animal or plant for subsequent detection of the marker or its metabolite in the organism itself or in its byproducts. The invention thus allows the organism and its byproducts to be identified and also allows for monitoring of the uptake or intake of any substance that is intentionally associated with the marker at the time of introduction to the organism.

The invention allows plants, animals and their byproducts (i.e., fruits, vegetables, meats, fish, poultry, eggs, wool) to be identified with respect to (1) country or region of origin for duty or trade monitoring purposes, (2) brand identity for substitution or quality assurance purposes, (3) differentiation between genetically modified and nongenetically modified products, (4) religious purposes, or (5) identity for any other purpose of ownership or origin.

Markers can also be used to monitor uptake or intake of a substance with which the marker is intentionally associated. For example, markers can be associated with agricultural chemicals such as pesticides or fertilizers prior to application and can be subsequently detected in plant tissues. This can be useful for determining liability for crop failures, for verifying a previous application prior to re-treatment, or for monitoring uptake levels of the substance in the plant.

Accordingly, in one aspect, the invention features a method of marking a living organism or its by-products for identification, by: (a) introducing a detectable compound into the organism by ingestion, injection, or uptake for the purpose of marking the organism, wherein the detectable compound or its metabolite passes into the tissue or by-products of the organism in detectable form; (b) after a period of time, following step (a), sufficient for passage of a detectable amount of the detectable compound or detectable metabolite into the tissue or by-products, collecting a sample of tissue or by-products; and (c) detecting the detectable compound or detectable metabolite thereof in the sample in order to identify the organism or its by-products.

In another, related aspect, the invention features a method of monitoring an oral therapeutic regimen in an animal, by (a) providing to the animal an orally active therapeutic compound and a detectable compound that passes through the digestive system and into the bloodstream, excretory system, or other tissue or body fluid in detectable form; (b) after a period of time, following step (a), sufficient for passage of a detectable amount of detectable compound into the body fluid or tissue, collecting a sample of the fluid or tissue from the animal; and (c) measuring or detecting the detectable compound or metabolite thereof in the sample, using specific binding pair-technology, (e.g., immunoassay), in which the detectable compound is one member of the specific binding pair, and the other member of the pair is used for detection. Preferably, the animal is a human patient who is self-administering the orally active compound, and monitoring is carried out (usually by the patient's physician) in order to assess therapeutic regimen compliance. As is discussed in greater detail below, such compliance is essential for drugs used to treat alcoholism and drug abuse, e.g., Naltrexone, and for drugs used to treat communicable, difficult-to-eradicate infections such as tuberculosis and HIV.

In other embodiments of the above method, the animal is a non-human animal such as a bird (chickens, turkeys), or a mammal such as the ungulate mammals, which include cattle and horses, to which orally active veterinary pharmaceuticals are administered, and which must be monitored.

The detectable compound and the orally active compound can be provided together, in separate unit dosage forms, or can be provided in a single orally administrable formulation such as a pill, tablet, capsule, or liquid. In some embodiments, the detectable compound labels the therapeutic compound, i.e., it is bonded (preferably covalently) to the therapeutic compound.

In another, related aspect, the invention features a method for monitoring oral ingestion of a first compound by an animal by (a) co-administering with the first compound a detectable compound in sustained release form, wherein the detectable compound passes through the animal's digestive system into the bloodstream excretory system or other tissue or body fluid in detectable form; (b) after a period of time, following step (a), sufficient for passage of a detectable amount of the detectable compound or detectable metabolite thereof into the tissue or body fluid, collecting a sample from the animal; and (c) detecting the detectable compound or metabolite in the sample as an indication of oral ingestion of the first compound. As in other aspects of the invention, the animal can be a human patient, and the first compound can be a therapeutic compound such as an antibiotic. Detection of the detectable compound in this aspect can be, but need not be, by specific binding pair technology, e.g., immunoassay. Other methods, e.g., fluorescence, UV emission, and IR spectroscopy can, alternatively, be used for detection and measurement. In this aspect of the invention, because the detectable compound is in sustained release form, measurement of the detectable compound in the sample provides a measure of the time elapsed between administration and measurement, or of the initial concentration of the first compound administered, or both. This aspect of the invention can be used in connection with non-human animals as well, e.g., birds and ungulate mammals.

In another, related aspect, the invention features a method of marking a living animal for later detection of the animal or component or derivative thereof, by (a) causing the animal orally to ingest a detectable compound that passes through the digestive system of the animal and into its bloodstream, excretory system, or other tissue or body fluid in detectable form; (b) after a period of time, following step (a), sufficient for passage of a detectable amount of the detectable compound or detectable metabolite thereof into the body fluid or tissue, collecting a sample of the fluid or tissue from the animal; (c) measuring or detecting the detectable compound or detectable metabolite thereof in the sample, wherein detection is by specific binding pair technology as described above.

Similarly, the method can be used to mark a living plant for later detection of the plant or portion or derivative thereof, involving (a) maintaining the plant in a solid or liquid medium which includes a detectable compound which is taken up by the plant, and (b) after a period of time, following step (a), sufficient for uptake by the plant of a detectable amount of the detectable compound, assaying the plant or a derivative thereof for the detectable compound, wherein the detectable compound is measured using specific binding pair technology as described above.

An alternative form of this aspect of the invention involves applying (e.g., by spraying) a detectable compound onto the plant such that it is absorbed by the plant for later detection. This aspect of the invention is useful, e.g., for distinguishing transgenic organisms from non-transgenic ones, where the visually observable phenotypes of the two are the same.

In another aspect, the invention provides a method for measuring or determining whether a bioactive compound has been taken up or absorbed by a plant, by (a) prior to said uptake or absorption, associating with the bioactive compound a detectable compound which, when it enters the plant, does so in detectable form; and (b) following uptake or absorption, assaying the plant or derivative thereof for the detectable compound or a detectable metabolite thereof, wherein detection is carried out using specific binding pair technology as described above. This aspect of the invention is particularly useful for detecting or measuring in plants compounds such as pesticides, herbicides, and fertilizers, which are undesirable in plant tissues in amounts above certain established levels. In this aspect of the invention, as in others, the bioactive compound and the detectable compound can be associated together, or can be covalently bonded.

In the animal counterpart aspect of the invention, an orally ingested bioactive compound is monitored in an animal, by (a) providing the bioactive compound associated with a detectable compound that passes through the digestive system of the animal and into the bloodstream, excretory system, or other tissue or body fluid in detectable form, causing the bioactive compound and the detectable compound to be ingested together by the animal; (b) after a sufficient period of time for the detectable compound, to pass through the digestive system of the animal into the bloodstream, excretory system, or other body fluid or tissue, obtaining a sample of body fluid or tissue of the animal; and (c) measuring or detecting the detectable compound or detectable metabolite thereof in the sample, using specific binding technology. In this aspect, the bioactive compound can be a veterinary pharmaceutical or a feed additive which is to be monitored.

The sustained release formulation of the detectable compound is advantageous for several reasons. One advantage is that the detectable compound or detectable metabolites thereof can be quantatively measured, whereby the amount of the detectable compound measured is indicative of the time elapsed between administration and measurement, or of the initial concentration of the first compound administered, or both. By altering the encapsulation conditions of the sustained release marker, the absorption and excretion rates of the marker(s) can be altered to meet the requirements of different types of monitoring programs. Many suitable sustained release methods and formulations are well known in the art.

The invention can be used not only to monitor compliance with therapeutic regimens for pharmaceuticals, it can also be used to ensure authenticity of urine samples which are tested for drugs of abuse; the person whose urine is to be tested for the presence of the subject drug or metabolite thereof ingests one more detectable compounds at a defined time prior to submission of the urine sample; presence of the detectable compound or metabolite thereof in the urine confirms authenticity of the sample.

In all aspects of the invention, preferred detectable compounds are substances which are in the category "generally recognized as safe" (GRAS). Thus, in most instances the use of the invention to monitor drug regimen compliance or authenticate urine samples does not complicate therapy with potentially toxic additional compounds, nor does it add expensive and time-consuming regulatory barriers. The invention allows the presence of many drugs to be detected using a simple analytical method that a physician can perform quickly during an office visit. The invention also permits the monitoring of drugs which are fast-acting and which have short half lives, and which are thus difficult, under current regimens, to detect and measure accurately. Further, the invention in some instances permits easy-to-obtain urine samples to be used to detect drugs which normally can be measured only in serum because they do not pass into the urine. The invention also in many cases can lower the cost of drug testing.

As is mentioned above, one class of complementary binding pair systems which can be used to detect detectable compounds or detectable metabolites of those compounds are antigen/antibody systems, which are well known in the art. The antigen, in this case, is or includes the detectable compound, which can be a hapten which is ionically or covalently bonded to the drug, or can be a hapten or larger detectable compound which is co-administered with the drug. Other examples of complementary binding pairs are lectin/carbohydrate; avidin/biotin; receptor/ligand; and molecularly imprinted polymer/print molecule. One advantage of using complementary binding pair technology to measure the detectable compound is that this technology can be very sensitive, in the part-per-billion range, and it can be used with practically any drug regardless of whether there is a direct method for detecting the drug. Thus, compounds which are already approved for use in foods and pharmaceuticals can be used as very sensitive marker compounds, in combination with specific antibodies to those compounds. These GRAS detectable compounds can be selected for particular characteristics they exhibit following ingestion, e.g., compatibility with the drug of interest, long half-life, and extended excretion into the urine.

The invention provides physicians with information critical in assuring that medications are being taken properly (e.g., the prescribed dose per unit time), and that any changes in dosage or treatment are prescribed for the appropriate therapeutic reason, rather than because the correct information has not been obtained regarding compliance with oral self-administration instructions.

The invention can also be used to mark veterinary products as an aid in determining the level of treatment that an animal is receiving. As compliance is not an issue in veterinary applications of the invention, the invention assures that the proper level of a given medicinal is being administered.

Other features and advantages of the invention will be apparent from the following description of the preferred embodiments thereof and from the claims.

DETAILED DESCRIPTION

The invention makes use of a number of components, which are described below in greater detail.

Detectable Compounds

Where the detectable compound is in sustained release form, it may, according to the invention, be any non-toxic substance detectable by any means, including specific binding pair techniques, fluorescence, color, spectroscopic methods, or NMR. Compounds that can be detected by non-immunological means such as fluorescence, UV emission, or IR spectroscopy are, e.g., riboflavin, albumin, and salicilates, some of which are described (along with standard methods for their detection) in the AOAC International Handbook, hereby incorporated by reference. Where the detectable compound is not in sustained release form, detection is achieved using specific binding pair methodology, which provides highly sensitive, quantitative information.

Many non-toxic haptens can be used for detection, either immunologically or by other means. Where immunologic detection is used, antibodies to the hapten are produced using standard methods, i.e., by coupling the hapten to a carrier such as albumin to form an immunogen and immunizing a rabbit or mouse with the immunogen to elicit the generation of, respectively, polyclonal or monoclonal antibodies specific for the hapten.

Examples of haptens that can be detected immunologically are beta lactams, sulfa drugs, tetracyclines and aminoglycosides; and drugs of abuse, such as opiates, cocaine, and amphetamines.

Other haptens suitable for use in the present invention are described in Garner et al. U.S. Pat. No. 5,429,952, hereby incorporated by reference. In addition, the '952 patent describes in detail methods for the use of haptenic markers, in another context, and also describes their detection by immunological means. Some of the material from the '952 patent is reproduced, sometimes in paraphrased form, below for the convenience of the reader. The low molecular weight haptens usefull in the present invention are, as is mentioned above, of acceptably low toxicity, and inert with respect to the product marked. The hapten should be one which is not normally present in the compound being marked, i.e., it should not be a by-product of the production process, or a normal impurity or standard additive for the product.

Examples of suitable haptens useful as labels in the invention are listed below in Table 1 (which has been taken from the '952 patent).

TABLE 1

| MARKER CHEMICALS TO WHICH ANTIBODIES PAIRS HAVE BEEN GENERATED | |
|---|---|
| Erythrosine | Chromotrope FB |
| 4-Aminoaphthalene-1-sulphonic acid | Ponceau 4R |
| Amaranth | Ponceau S |
| Dofcol Brown | 4'-disulphonic acid |
| 4-Amino-1, 1-azobenzene-3,4'-disulphonic acid | Tropaelin O |
| Mordant yellow 7 | Curcumin |
| 4-Hydroxy-3-methoxycinnamic acid | Coniferyl alcohol |
| 4-Hydroxy-3-methoxyphenyl-3-buten-2-one | Hexyl vanillate |
| Vanillin | Acetovanillone |
| Ethyl-4-hydroxy-3-methoxycinnamic acid | |
| 7-Amino-4-methylcoumarin | |

In some instances it may be necessary to purify, at least partially, the hapten prior to detecting it by immunological or other means. Such purification can involve filtration to remove solids, solvent extraction of the marker; evaporation to concentrate the marker; and solid phase extraction of the marker, e.g., using ion exchange, silica, or other chromatography.

In some instances, more than one marker can be employed. The markers may be simply detected (so that a positive or negative result is obtained), or the markers may be quantitated, providing more information than a simple on-off test.

Immunologic methods for detecting markers are standard, and can take the form of competitive enzyme-linked immunoabsorbent assay (ELISA). Other standard immunoassay formats can be used as well, including enzyme-mediated immunoassay, sandwich immunometric assays, and lateral flow assays. Examples of enzymes used in such assays are horseradish perioxidase and alkaline phosphatase. Substrates useful in these assays include o-phenylenediamine dihydrochloride. Other indicators such as colloidal gold or dyed latex particles also can be used. In some instances, a measuring device such as a spectrophotometer or fluorometer may be used.

The antibodies used in the assays are produced by standard techniques, in which the hapten is conjugated to a larger molecule such as albumin, and the resultant complex used to immunize the animal which will produce the antibody.

The invention provides time release markers which can be used in assays assuring that patients enrolled in clinical trials of new drugs that have not yet received federal approval take their medication as directed. Multicenter clinical trials are very expensive and require a great deal of time and resources. Noncompliance by patients in new drug clinical trials is believed to be responsible in some instances for poor drug efficacy and in the nonapproval by the Food and Drug Administration of otherwise effective and useful drugs. Therefore, noncompliance by patients enrolled in clinical trials can cost pharmaceutical companies millions of dollars in research and development and clinical testing costs and also cost the public by preventing approval and use of safe, efficacious drugs.

When a time-release marker is ingested along with the medication, then the marker can be assayed using either direct detection, or by using indirect detection such as a competitive enzyme immunoassay or competitive fluorescence immunoassay. The level of marker in the blood, urine, or saliva correlates to a specified level of the drug in the bloodstream. If too much drug was taken, then higher-than-expected levels of the marker are detected. If too little drug was taken by the patient, then lower-than-expected levels of the time-release marker are detected. These markers can be encapsulated in time release capsules and taken with the prescribed medication. Preferably, they are provided in one capsule, to circumvent the need to take two tablets, making it simpler for the patient to maintain compliance.

Haptens Excreted in Urine

Some of the hapten markers of the invention must not only be safe to ingest but also available in the plasma or urine for sampling. Urine testing for the presence of the marker hapten is safe and noninvasive, and is therefore the preferred matrix for assaying the marker hapten. Two examples of marker haptens that are available for sampling both in the blood and the urine are vitamin C (ascorbic acid), and vitamin B2 (riboflavin).

Vitamin C

Vitamin C is an essential water-soluble vitamin that is readily absorbed from the gastrointestinal tract into the bloodstream and excreted in the urine. A number of studies have measured plasma concentrations of vitamin C in the plasma of humans (Yew, M. S., 1984, *Nutr. Rep. Int.* 30:597–601; Melethil, S. et al., 1987, *Ann. N.Y. Acad. Sci.* 498:491–493) and the urine of test subjects orally ingesting small to large daily doses of vitamin C (Hornig, D. et al., 1980, *Int. J. Vitam. Nutr. Res.* 50:309–314; Melethil, S. et al., 1987, *Int. J Pharmaceut.* 31:83–89).

Vitamin B2

Vitamin B2 (riboflavin) has also been assayed extensively in the urine of human patients after oral ingestion using a fluorometric method developed in the late 1950's. (Hobby, G. L. et al., 1959, *Am. Rev. Resp. Dis.* 80:415–423; Fuller, R. K. et al., 1979, *Ann. Int. Med.* 90:901–904; Fuller, R. et al., 1983, *J Chron. Dis.* 36(2):161–170). Quantitative measurements of the marker are possible using small doses of riboflavin ingested during courses of treatment for nonvitamin-deficiency disorders. Levels of riboflavin above those naturally found in the urine of patients can be determined quantitatively. In addition, riboflavin can be added to a tablet formulation without adversely affecting the potency of the medication (Fuller, R. et al., 1983, *J. Chron. Dis.* 36(2):161–170).

Labeling

Although it is preferred that the active agent and the marker be admixed, but not reacted with each other, it is also possible to label the agent with the marker. The requirements for labeling a pharmaceutically active agent with any detectable GRAS agent (time-release or non-time-release) are as follows:

1) the chemical bond between agent and label must be one which does not inactivate the agent, and which can be formed under non-inactivating conditions;
2) the agent/label bond preferably is cleavable under physiological conditions, so that in the patient's body the label is released, preferably into the excretory or digestive system so that it can be detected or measured in the urine or saliva;
3) the label, or a metabolite of the label, must be detectable following the physiological processing that occurs following ingestion;
4) the label and its metabolites must exhibit acceptably low toxicity.

Pharmacologically Active Compounds

The methods of the invention can be used to monitor treatment regimen compliance for any drug which is administered orally. Generally, such drugs fall into the following categories: antibiotics; synthetic anti-viral and other anti-pathogen small organic molecules; compounds used to treat neoplasms (e.g., cancer); anti-inflammatory compounds; immunosuppressive compounds; compounds for treatment of symptoms of infectious and non-infectious illnesses; compound used in conjunction with alcohol or drug dependence therapy (such as Naltrexone); compounds which are orally administered to provide diagnostic information; and drugs with the potential for abuse. In more detail, these categories of compounds can be described as follows.

Antibiotics

The invention is particularly useful for monitoring regimen compliance for antibiotics used to treat diseases, e.g., tuberculosis and Lyme disease, where symptoms may be relieved after a short period of treatment, but prolonged treatment is nonetheless required for complete eradication of the pathogens.

Examples of antibiotics that can be monitored according to the invention are vancomycin, penicillin, erythromycin, and amoxycillin.

Synthetic Anti-Pathogens

Many synthetic small organic molecules which are orally administered to treat viral and fungal diseases, for which strict compliance is crucial for therapeutic success. Examples are protease inhibitors for HIV treatment; anti-herpes compounds such as Acyclovir® and Famvir®; and anti-fungal compounds such as ketoconazole.

Anti-Cancer Drugs

A number of anti-cancer drugs are prescribed for home oral self-administration; it is essential that these drugs, which often cause unpleasant side effects, be taken as prescribed. Examples are peptide hormone analogs such as Sandostatin®. Non-peptide examples are Actinomycin-D, Doxorubicin, Fluorouracil and Mitomycin.

Anti-Inflammatories

A number of anti-inflammatory agents are long-acting and must be maintained at therapeutic levels in the bloodstream for optimal efficacy; one example is Indomethocin®, a non-steroidal compound. Steroidal anti-inflammatory agents such as prednisone also are administered orally, and must be ingested according to strict regimens.

Immunosuppressive Agents

Patients such as allograft (e.g., kidney, lung, and heart) recipients and patients suffering from autoimmune diseases such as Systemic Lupus Erythmatosis (SLE) and rheumatoid arthritis (RA) are frequently prescribed long-acting oral immunosuppressive agents such as cyclosporin and FK506. Monitoring of compliance with prescribed self-administration regimens is essential for these patients to prevent morbidity and minimize healthcare costs associated with SLE and RA.

Symptom-Treating Drugs

Many orally-administered small molecules are used to treat the symptoms (e.g., pain, hypertension, arrythmia, anxiety, depression, sinus congestion) associated with medical conditions, both pathogen and non-pathogen-related. Some of these, particularly anti-hypertensives such as beta blockers (Inderol®, for example) and depression-treating drugs (e.g., Prozac®, Paxil®) are optimally effective when a prescribed serum concentration is reached and maintained, rendering patient compliance essential.

Drug Dependence Therapy

One drug, Naltrexone, used to treat alcohol dependence is usefully monitored (with, e.g., time-release riboflavin) according to the invention. Other such drugs are disulfiram and acampresate,.

Diagnostic Compounds

A number of compounds are orally administered so that their interaction with the patient's endogenous chemistry can be observed to yield diagnostic information. For the readout of such tests to be meaningful, compliance with the prescribed administration regimen is necessary. Examples of such diagnostic agents are insulin and glucose.

Drugs of Abuse

The methods of the invention can render the detection in urine, saliva, or blood of drugs of abuse (e.g., opiates, amphetamines, cannabinoids and tranquilizers) or their metabolites easier and more reliable. Each prescription drug can be routinely provided with a different detectable label, for which standardized detection technology is available.

EXAMPLES

Monitoring of Naltrexone with Riboflavin

Since the mid 1980's, there has been increasing interest in the use of Naltrexone hydrochloride as an adjunct in treating alcohol dependence. Naltrexone, when administered in conjunction with behavioral treatment, can reduce alcohol consumption. (O'Brien et al., 1996, *Alcohol* 13(1): 35–39) Thus, it is reasonable to assume that the effectiveness of Naltrexone may be improved by a treatment program that enhances medication compliance.

Naltrexone compliance can be enhanced according to the invention by the use of the time-release GRAS marker riboflavin ingested with the medication. Three methods, generally, can be used to co-administer time-release riboflavin and Naltrexone:

1) orally administer, concurrently, Naltrexone and riboflavin in separate oral formulations, e.g., capsules or tablets (the Naltrexone and riboflavin formulations are identical in appearance, so that the patient cannot elect to take only the riboflavin and not the Naltrexone);

2) orally, administer the riboflavin and Naltrexone together in a single formulation, e.g., a single tablet or capsule containing both components homogeneously dispersed within a standard pharmaceutically acceptable excipient;

3) orally administer a single formulation in which Naltrexone is labeled with riboflavin covalently bonded to the Naltrexone.

For separate administration, Naltrexone is provided in standard orally administratable tablets, e.g., as available in 50 mg/tablet dosage form from duPont. Sustained release tablets of riboflavin are prepared using conventional methods used in the preparation of sustained release, orally-administered small molecules. Preferably, the tablets are formulated (color, size, shape) to be identical in appearance and weight to 50 mg Naltrexone tablets, to discourage self-administration of the sustained-release riboflavin but not the Naltrexone.

The prescribing physician instructs the patient to orally ingest one of each tablet, together, every 24 hours. After 3–7 days, the patient provides a urine sample to the physician or associated clinic. Riboflavin concentration in the urine is measured using standard fluorescence-based methods, such as a tube or microwell fluorometer with excitation and emission filters set for riboflavin.

The concentration of riboflavin in the urine sample provides an indication of whether the patient has ingested the Naltrexone, and whether the medication was self-administered as prescribed, i.e., in the dosage and at the time(s) prescribed.

The regimen just described is made possible by the sustained release riboflavin formulation, which addresses the short serum half-life of unformulated riboflavin. Unformulated riboflavin has been used to determine compliance with other drugs, such as disulfiram, but only crude qualitative methods could be performed, having limited clinical value (Fuller et al., *J. Chron. Dis., Vol.* 36(2): pp. 161–170 (1983)).

As is described above, it is preferable that Naltrexone and time-release riboflavin be provided in a single oral formulation, e.g., a tablet or liquid containing both components.

The formulation can be produced such that both components are in time-release form, or so that only the riboflavin is so formulated. Standard methods can be used, in conjunction with the time-release riboflavin formulation described above, to produce tablets or suspensions of either formulation.

Penicillin Labeled With Riboflavin

Penicillin is a member of a class of low molecular weight antibiotics produced by molds of the genus Penicillium. Although these antibiotics have different R-groups attached to their six membered rings, they all contain a stressed beta-lactam ring. The penicillins are very inexpensive to produce and are widely prescribed because they have a strong antimicrobial effect upon human and animal pathogens such as staphylococci, gonococci, pneumococci, and some meningococci. The therapeutic effects of penicillins are diminished by not following prescribed dosage and time intervals between ingestion. Therefore, an easy method to measure compliance could prevent highly morbid or fatal infections.

Penicillins can be labeled with a marker hapten using covalent coupling chemistry. The primary amino group (—NH2) of the penicillin is covalently linked to a homobifunctional or heterobifunctional linker in buffered saline at neutral pH with agitation for one hour at room temperature. Riboflavin is labeled in a similar fashion, and the two molecules are then combined and allowed to covalently react with agitation for one hour at room temperature. Penicillin molecules coupled with riboflavin are then passed through a molecular sieve column at room temperature or at 4° C.; unlabeled antibiotics and riboflavin are physically separated from the larger conjugated antibiotic and discarded. Conjugated molecules are collected and concentrated. After ingestion by the patient, conjugated drugs that are excreted in the urine are then assayed using a competitive immunoassay format to semiquantitatively determine their concentration. Either a competitive fluoroimmunoassay or competitive colorimetric assay may be used to detect the conjugate in urine. The levels can then be correlated to the true amount of antibiotic in the patient.

Acyclovir and Vitamin C

Acyclovir® (acycloguanosine) is a nucleoside antiviral agent that specifically inhibits in vivo reproduction of herpes viruses, a class of icosahedral, double stranded DNA viruses. This viral group includes oral and genital herpes simplex viruses (Types 1 and 2, respectively), cytomegalovirus, and *Herpes zoster*, the cause of shingles. The phosphorylated derivative of acyclovir produced by the virus-induced thymidine kinase enzyme inhibits the virus-induced DNA polymerase. Acyclovir® is effective in preventing recurrences of herpes simplex viral outbreaks, but the prescribed dose and time of ingestion must be followed closely and all medication must be taken as prescribed. Only 3% of the drug becomes therapeutically available. Therefore, a method to monitor compliance with this drug is important. The Acyclovir® molecule is administered with Vitamin C, some of which is excreted in the urine or saliva of the patient and collected for measurement.

Mytomycin C and Riboflavin

Mytomycin C is a major antitumor antibiotic used to treat leukemias, cancers of the stomach, pancreas, bladder, breast, cervix, esophagus, gallbladder, head and neck and lung. The drug is also called mitomycin and mutamycin. During treatment the drug causes nausea, vomiting, loss of appetite, fever, chills, sore throat and burning at the injection site, and to a lesser extent, hair loss, fatigue, and diarrhea. These side effects make drug compliance difficult. A marker hapten combined in a single dosage with mytomycin C could be used to monitor compliance. The marker, e.g., riboflavin, would be excreted in the urine and collected for immunoassay using a colorimetric instrument, such as a spectrophotometer (also called an ELISA reader). The amount of marker hapten in the urine or saliva would be detected using a competitive immunoassay. The degree of marker hapten present would be determined using an enzyme conjugate (such as alkaline phosphatase) and complimentary chromagenic substrate, (such as ABTS). The patient sample containing the marker hapten (500 µL) is added to tube (or microwell) coated with an antibody specific for the marker hapten, immediately followed by 500 µL of an enzyme conjugate labeled with the marker hapten. A standard, composed of a known amount of marker hapten and enzyme conjugate is also prepared at the same time. The solutions are mixed then allowed to incubate for about 5 min. The tubes are washed 3 to 5 times with wash solution, then 500 µL of substrate is added and the tubes mixed, then incubated for 5 min. During this time the enzyme conjugate bound to tube reacts with the added substrate, converting it into a colored product. After 5 min., the reactions are stopped using 500 µL of a stop reagent such, as weak sulfuric acid or an enzyme inhibitor. The amount of color in each tube is inversely proportional to the amount of marker hapten present. The patient sample is then compared to the standard tube with the known amount of marker hapten.

Cyclosporine and Time-Release Vitamin C

Cyclosporine (also called cyclosporin, CsA, and Sandimmune) is an immunosuppressant agent used in bone marrow transplantation. It is typically administered intravenously with other drugs to reverse multidrug resistance. The drug causes numerous side-effects, such as headache, tremor, hypertension, and kidney problems, and to a lesser extent diarrhea, nausea and vomiting, confusion, and depression. Close monitoring of patients for drug compliance would also greatly benefit the patient and provide the physician a measure of how well the medication is working. A time-release formulation of marker hapten such as Vitamin C administered with the cyclosporine would allow long-term surveillance of patients for compliance with prescribed medications. In this example, the marker hapten is enclosed in compounds specially formulated to slowly dissolve in the gastrointestinal tract. The specially formulated, digestive acid-resistant compounds could be in the form of tiny capsules of various thickness. As the compounds slowly dissolve over many hours, they would release constant quantities of the marker hapten, which then circulates in the bloodstream and then is excreted in the urine for collection and detection, as described in earlier examples.

Marking a Plant for Subsequent Identification

Incorporation of a proprietary marker into a plant provides a means for the subsequent identification of the marked plant. This information can be used to determine the origin of the plant, such as the grower or distributor, or whether the plant represents a genetically modified organism.

The following example illustrates uptake of a detectable marker by an Orchid. A live orchid is placed in a flask containing 250 ml of water so that the cut stem is immersed in the water. Another orchid is placed in a similar flask in which the water contains 500 µg/ml of the marker 4-amino-1,1-azobenzene-3,4'-disulphonic acid. After six hours, both plants are removed from their respective flasks and analyzed for the presence of the marker using a simple lateral flow diagnostic test specific for the marker. A 2.0 g sample of stem is taken from a point above the level that was immersed in the water. Each sample is ground with 2.0 ml of water using a mortar and pestle. The respective extracts are tested using a simple lateral flow immunodiagnostic device specific for the marker. Three hundred microliters of respective stem extracts are added to the sample well of respective lateral flow devices that have the sensitivity to detect the specific marker at levels of 100 ng/ml and higher. Within 5 to 10 minutes, the visual results observed on the lateral flow assay devices (formation of 1 visible line on the device) indicate the presence of marker in the stem extract from the orchid held in the marked water, whilst analysis of stem material from the control orchid shows no marker (formation of two visible lines on the device). Thus by marking the water that the plant subsequently takes up, it is possible to introduce markers systemically into the plant.

What is claimed is:

1. A method of monitoring a therapeutic regimen in an animal, said method comprising
   a) providing to said animal a therapeutic compound and a detectable compound that passes into the bloodstream, excretory system, or other tissue or body fluid in detectable form;

b) after a period of time, following step (a), sufficient for passage of a detectable amount of said detectable compound into said body fluid or tissue, collecting a sample of said fluid or tissue from said animal; and c) measuring or detecting said detectable compound, or a detectable metabolite thereof, in said sample, wherein said detectable compound comprises one member of a specific binding pair, and detection is carried out using the second member of said specific binding pair.

2. The method of claim 1, wherein said animal is a human patient.

3. The method of claim 1, wherein said therapeutic compound and said detectable compound are self-administered, and said monitoring is carried out in order to assess therapeutic regimen compliance.

4. The method of claim 1, wherein animal is a non-human mammal.

5. The method of claim 4, wherein said mammal is an ungulate mammal.

6. The method of claim 1, wherein said therapeutic compound is a veterinary pharmaceutical.

7. The method of claim 1, wherein said detectable compound is in sustained-release form.

8. The method of claim 1, wherein said therapeutic compound and said detectable compound are contained in a single orally-administrable formulation.

9. The method of claim 8, wherein said detectable compound is covalently bonded to said therapeutic compound.

10. The method of claim 1 wherein said detectable compound is a hapten and the second binding pair member is an antibody specific for said hapten.

11. The method of claim 1, wherein said therapeutic compound is covalently bonded to said detectable compound.

12. The method of claim 1, wherein said therapeutic compound is orally active, and said detectable compound passes through the digestive system of the animal in detectable form.

13. A method for monitoring oral ingestion of a first compound by an animal, said method comprising a) co-administering with said first compound a detectable compound in sustained-release form, wherein said detectable compound passes through the animal's digestive system into the bloodstream, the excretory system, or other tissue or body fluid in detectable form;

b) after a period of time, following step (a), sufficient for passage of a detectable amount of said detectable compound or detectable metabolite thereof into said tissue or body fluid, collecting a sample of said fluid or tissue from said animal; and c) detecting said detectable compound or metabolite in said sample as an indication of oral ingestion of said first compound.

14. The method of claim 13, wherein said detectable compound comprises one member of a specific binding pair, and detection of said detectable compound is carried out using the second member of the specific binding pair.

15. The method of claim 13, wherein said first compound and said detectable compound are admixed together in one orally administratable formulation.

16. The method of claim 13, wherein, in step (c), said detectable compound is measured, the amount of said detectable compound being indicative of the time elapsed between administration and measurement, or of the initial concentration of said first compound.

17. The method of claim 13, wherein said animal is a non-human mammal.

18. The method of claim 17, wherein said mammal is an ungulate mammal.

19. The method of claim 13, wherein said animal is a human patient.

20. The method of claim 13, wherein said first compound is a therapeutic compound.

21. A method for authenticating a urine sample obtained from a patient whose urine is to be tested for the presence of a drug or metabolite thereof, said method comprising a) determining the point in time at which a urine sample is to be collected from said patient, b) orally administering to said patient a detectable compound that passes through the human digestive system and into the urine in detectable form, at a time prior to the predetermined urine collection time sufficient for passage of a detectable amount of said detectable compound or detectable metabolite thereof into the urine of said patient, c) collecting a urine sample from said patient at the predetermined time; and d) detecting said detectable compound or detectable metabolite thereof in said collected urine sample as an indication of authenticity, wherein said detectable compound, or detectable metabolite thereof, comprises one member of a specific binding pair, and said detecting is carried out using the second member of said specific binding pair.

22. The method of claim 21, wherein said detectable compound is provided to said patient in sustained-release form.

23. A method of marking a living animal for later identification of the animal or component or derivative thereof, said method comprising a) causing the animal orally to ingest, or injecting into the animal, a detectable compound that passes into its bloodstream, excretory system, or other tissue or body fluid in detectable form;

b) after a period of time, following step (a), sufficient for passage of a detectable amount of said detectable compound into said body fluid or tissue, collecting a sample of said fluid or tissue from said animal; and c) measuring or detecting said detectable compound, or a detectable metabolite thereof, in said sample, wherein said detectable compound comprises one member of a specific binding pair, and detection is carried out using the second member of said specific binding pair.

24. The method of claim 23, wherein said animal is a transgenic animal.

25. A method of monitoring an orally ingested bioactive compound in an animal, said method comprising a) providing said bioactive compound associated with a detectable compound that passes through the digestive system of the animal and into the bloodstream, excretory system, or other tissue or body fluid in detectable form;

b) causing the bioactive compound and the detectable compound to be ingested together by the animal;

c) after a sufficient period of time for the detectable compound to pass through the digestive system of the animal into the bloodstream, excretory system, or other body fluid or tissue, obtaining a sample of body fluid or tissue of said animal; and d) measuring or detecting said detectable compound, or a detectable metabolite thereof, in said sample, wherein said detectable compound comprises one member of a specific binding pair, and detection is carried out using the second member of said specific binding pair.

26. The method of claim 25, wherein said bioactive compound is a veterinary pharmaceutical.

* * * * *